March 21, 1961 W. E. LAMMERTS Plant Pat. 2,036
ROSE PLANT
Filed June 20, 1960
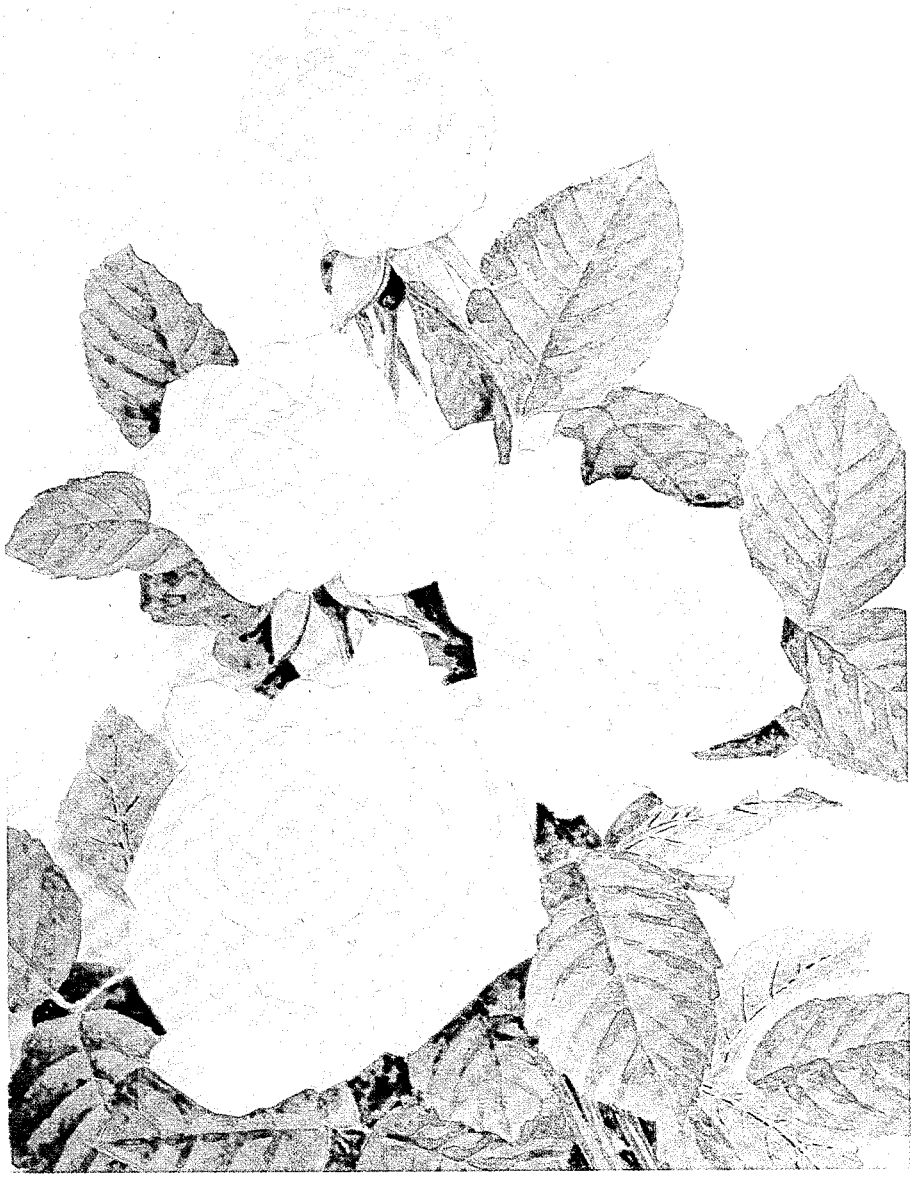
WITNESS
Addison E. Avery
INVENTOR
WALTER E. LAMMERTS
by Rummler & Snow
ATTYS.

United States Patent Office

Plant Pat. 2,036
Patented Mar. 21, 1961

2,036

ROSE PLANT

Walter E. Lammerts, Livermore, Calif., assignor to Amling-De Vor Nurseries, Inc., Livermore, Calif., a corporation of California Filed June 20, 1960, Ser. No. 37,537

1 Claim. (Cl. 47—61)

This invention concerns a new and distinct variety of rose plant of the hybrid tea class and was originated in 1956 as a seedling resulting from breeding procedures carried on by me and under my direction, commencing in May 1953, at Livermore, California.

My new variety is a cross of Queen Elizabeth (Plant Pat. 1,259) and Tawny Gold (Plant Pat. 950) and continuous asexual propagation of the new variety by budding, since 1956, at Livermore, California, under my supervision, has proved the new variety to reproduce true to form.

Among the objects of my invention was that of producing a hot house variety having the vigor of Queen Elizabeth and the color of Tawny Gold; and additionally, I sought to obtain the foliage qualities of Queen Elizabeth together with an improved bud form and open flower form as compared with the qualities of the two parents.

These objectives have been accomplished in the new variety which is a tall compact, growing bush having abundant foliage with large leaves and which blooms continuously and profusely from spring through fall with medium size flowers having substantially the color of Tawny Gold. Under glass the new variety also blooms in winter, with a flower production comparable to Better Times (Plant Pat. 23).

The accompanying illustration shows my new variety of rose plant in full color and includes foliage as well as blooms in various stages of development. The colors shown are substantially true to the color designations hereafter set out.

The following is a detailed description of my new variety of rose plant and further distinctive features of my invention will be apparent therefrom. Color designations are according to British Colour Council Horticultural Color Chart.

*The plant*

Parentage:
- *Seed parent.*—Queen Elizabeth (Pl. Pat. 1259).
- *Pollen parent.*—Tawny Gold (Pl. Pat. 950).

Classification:
- *Botanic.*—Hybrid tea.
- *Commercial.*—Hot House rose.

Form: Tall compact bush.

Height: 5 to 6 feet.

Growth: Fairly rapid and vigorous. Strong, upright, and sturdy but slender growth.

Branching: Branches readily from cut flow base with remarkably erect growth of new shoots.

Foliage: Abundant, with many leaves close together on stem.
- *Size of leaf.*—Large, 7 inches long x 5 inches wide.
- *Shape.*—Wide and medium long, with serrated edges.
- *Textures.*—Leathery, with semi-glossy, smooth surface.
- *Color.*—Upper side, Parsley Green (00962). Under side, Lavender Green (000761 to 000761/2).
- *Leaflets.*—Large, to 2¾ inches long x 2 inches wide; usually 5 and occasionally 7 in number.

- *Petioles.*—Length, 1 to 1¼ inches. At base of leaflets, petioles are short—about ⅛ inch.
- *Ribs and veins.*—Fairly prominent and of lighter green, rather heavily tinged with authocyanin pigment toward base of leaflets.
- *Rachis.*—Grooved on top side, usually one small spine. (Sometimes 2 or more on bottom side.)
- *Thorns.*—Yes. Practically no prickles. Sizes.—⅜ to ⅝ inch. Color.—Light Lettuce Green (861/3).

*Bud*

Form: Long—urn shaped.

Size: Medium large. 1¼ to 1¾ inches long—⅝ to ¾ inch wide.

Opens: Slowly and very evenly with high centered spirally imbricated petal arrangement.

Color: When sepals first divide—Orpiment Orange (10/2). When sepals begin to unfurl—Apricot (609/1).

Sepals: Clasping. Remain around bud until petals begin to unfurl. Curl back as petals open.
- *Shape.*—Spear shaped. Every other sepal much laciniated, two without laciniations.
- *Color.*—Inside—Lavender Green (00761/2). Outside—near Scheeles Green (860/1).

Calyx: Pear shaped. Does not split.
- *Size.*—Medium large and broad.
- *Aspect.*—Smooth.

Peduncle: Length—4 to 6 inches.
- *Aspect.*—Smooth.
- *Strength.*—Erect, slender and wiry.
- *Color.*—Scheeles Green (860/1).

*Flower*

Blooming habit: Continuous and profusely from spring through fall. Under glass, also blooms in winter with production comparable to that of Better Times.

Size: Medium.
- *Diameter.*—4 to 4½ inches.
- *Depth.*—2¼ to 2½ inches.

Borne: Singly. Average stem length substantially the same as Better Times.

Shape: High center. Form does not change as bloom ages.

Petalage: 45 to 55 petals.
- *Arrangements.*—Imbricated.
- *Form.*—Regular. Not serrated.
- *Color.*—Outer petal—Empire Yellow (603/3); slightly darker (603) at base. Inside petal—Apricot (609/1) to Egyptian Buff (407). Reverse side—Buttercup Yellow (5) at base to Egyptian Buff (407). Petals stay on stem 6 to 8 days.

Petaloids: Number, variable, 6 to 10.
- *Sizes.*—⅜ inch wide x ½ inch long to ½ inch x ¾ inch.
- *Color.*—Buttercup Yellow (5) at base to Tangerine Orange (9/1). General color effect of newly opened flower is Apricot (609/1) to Egyptian Buff (407).

Peduncle: Length, 4 to 6 inches. Sturdy and upright. Color—Scheeles Green (860/1).

Discoloration (after full bloom): Fades to Empire Yellow (603/1) at base and gradually to Amber Yellow (505/2) toward margins of petals.

Texture: Soft. Appearance—velvety.

Fragrance: Very slight.

Weather effect: Bloom fades more rapidly to Empire Yellow (603/1) in wet or hot weather.

Persistence: Petals drop off as bloom becomes aged.

Lasting quality: 4 to 5 days on plant. 4 to 5 days as a cut flower.

Disease resistance: Fairly resistant to mildew, as observed in the area of Livermore, California.

*Genital organs*

Stamens, anthers: Arrangement—irregular. Length—1/16 to 1/8 inch. Number—not determined—very many.
Filaments: Color—Empire Yellow (603). Length—1/4 to 1/2 inch.
Pollen: Color—Empire Yellow (603).
Pistils: Number—40 to 50. Length—1/4 to 3/8 inch.
Stigmas: Color—Empire Yellow (603).
Ovaries: Many—number not determined.

*Fruit*

Fruit is fertile. Shape is round.
Color at maturity: Buttercup Yellow (5) shaded with Egyptian Buff (407).

My new variety of rose plant most nearly resembles its pollen parent, Tawny Gold (Pl. Pat. 950). The new variety is distinguished from Tawny Gold, however, in several important respects. Generally the new variety is much taller and more compact in its habit of growth, whereas Tawny Gold is spreading in habit; the new variety is much more vigorous than Tawny Gold and produces more flowers per season, under comparable growing conditions; the bud of the new variety is more urn-shaped whereas the bud of Tawny Gold is medium-long ovoid; and under the same hot house growing conditions the blooms of the new variety have 45 to 55 petals and 6 to 10 petaloids while Tawny Gold has 15 to 25 petals and only 2 to 5 petaloids.

Further distinctive characteristics of my new variety, as compared with Tawny Gold, reside in the fact that the leaves of the new variety are not as long as those of Tawny Gold, i.e. about 7 inches as compared with 8 inches in Tawny Gold, for leaves of the same age. However, the leaflets of the new variety are closer together on the rachis and being more closely spaced on the flowering stems they give the effect of more adequately clothing the plant and flowering shoots than in the case of Tawny Gold. Also, under the same or similar hot house growing conditions the leaflets of my new variety show much more anthocyanin pigmentation at the base of the petiolules and along the rachis than do those of Tawny Gold which are practically devoid of pigmentation. Furthermore the thorns of the new variety do not slant downward at nearly the same angle as do those of Tawny Gold. Rather the thorns of the new variety are almost at right angles to the stem.

My new variety of rose is readily distinguished from Queen Elizabeth, its seed parent, by its color. Also, while the new variety is not as vigorous as Queen Elizabeth, it does not throw blind eyes and tend to go dormant under winter growing conditions as does Queen Elizabeth.

Among the particular advantages of my new rose variety are its high productivity, with an index of 7.9, as compared for instance with Better Times which has an index of 7 under similar growing conditions; and the fact that the flowers of the new variety keep better in vases, under normal room conditions, than those of either Tawny Gold or Better Times.

Having thus described my new variety of rose plant, I claim:

A new and distinct variety of hybrid tea rose plant, substantially as herein shown and described, characterized particularly by its high rate of bloom production which is continuous from spring through fall, the regular and high centered form of the blooms and the long urn-shaped form of the buds, the large number of petals and petaloids in each of the blooms as compared with the parent varieties, the tall and compact form of the plant and the abundant large sized leaves closely spaced on the flowering stems, and by its retention of the distinctive color characteristics of its pollen parent while adopting the advantageous foliage and vigorous growing characteristics of its seed parent.

No references cited.